United States Patent
Shin et al.

(10) Patent No.: US 10,765,668 B2
(45) Date of Patent: Sep. 8, 2020

(54) ORAL TABLET COMPOSITION COMPRISING DEXLANSOPRAZOLE, ORAL TABLET COMPRISING THE SAME AND METHOD FOR MANUFACTURING THE SAME

(71) Applicant: LOTTE FINE CHEMICAL CO., LTD., Ulsan (KR)

(72) Inventors: Kwang Il Shin, Gunpo-Si (KR); Kyung Yeol Park, Incheon (KR); Sang Youb Lee, Incheon (KR)

(73) Assignee: LOTTE FINE CHEMICAL CO., LTD., Ulsan (KR)

( * ) Notice: Subject to any disclaimer, the term of this patent is extended or adjusted under 35 U.S.C. 154(b) by 0 days.

(21) Appl. No.: 16/464,491

(22) PCT Filed: May 10, 2017

(86) PCT No.: PCT/KR2017/004785
§ 371 (c)(1),
(2) Date: May 28, 2019

(87) PCT Pub. No.: WO2018/097426
PCT Pub. Date: May 31, 2018

(65) Prior Publication Data
US 2019/0275023 A1    Sep. 12, 2019

(30) Foreign Application Priority Data
Nov. 28, 2016  (KR) .................. 10-2016-0159355

(51) Int. Cl.
*A61K 31/4439*    (2006.01)
*A61K 9/00*    (2006.01)
(Continued)

(52) U.S. Cl.
CPC ............ *A61K 31/4439* (2013.01); *A61K 9/00* (2013.01); *A61K 9/20* (2013.01); *A61K 9/2018* (2013.01);
(Continued)

(58) Field of Classification Search
CPC ........ A61K 31/4439; A61K 9/00; A61K 9/28; A61K 9/20; A61K 9/2018; A61K 9/2054;
(Continued)

(56) References Cited

U.S. PATENT DOCUMENTS

| 2011/0189271 A1 | 8/2011 | Lad et al. |
| 2012/0164233 A1 | 6/2012 | Bhargava et al. |

(Continued)

FOREIGN PATENT DOCUMENTS

| KR | 20130115593 A | 10/2013 |
| WO | 2013111149 A1 | 8/2013 |

OTHER PUBLICATIONS

International Search Report issued in International Application No. PCT/KR2017/004785 dated Aug. 28, 2017 (2 pages).
(Continued)

*Primary Examiner* — Trevor Love
(74) *Attorney, Agent, or Firm* — Osha Liang LLP

(57) ABSTRACT

The present invention relates to: an oral tablet composition comprising amorphous dexlansoprazole, mannitol having an average particle size of 100 to 400 μm, a disintegrating agent and a lubricant; an oral tablet comprising same; and a method for manufacturing same. The oral tablet composition, according to the present invention, exhibits excellent hardness, has a shortened disintegration time, and at the same time, may be used to provide an oral tablet having improved friability. In addition, according to the present invention, a dry direct compression method is used as the method for manufacturing the oral tablet, and thus an (Continued)

increase in production efficiency by simplifying the production process may be achieved.

10 Claims, 1 Drawing Sheet

(51) Int. Cl.
    *A61K 9/28*          (2006.01)
    *A61K 9/20*          (2006.01)

(52) U.S. Cl.
    CPC .............. *A61K 9/2054* (2013.01); *A61K 9/28* (2013.01); *A61K 9/2866* (2013.01); *A61K 9/2095* (2013.01)

(58) Field of Classification Search
    CPC ... A61K 9/2866; A61K 9/2095; A61K 9/2886
    See application file for complete search history.

(56) References Cited

U.S. PATENT DOCUMENTS

2012/0231073 A1    9/2012    Manne et al.
2014/0030328 A1    1/2014    Cifter et al.

OTHER PUBLICATIONS

Written Opinion issued in International Application No. PCT/KR2017/004785 dated Aug. 28, 2017 (7 pages).

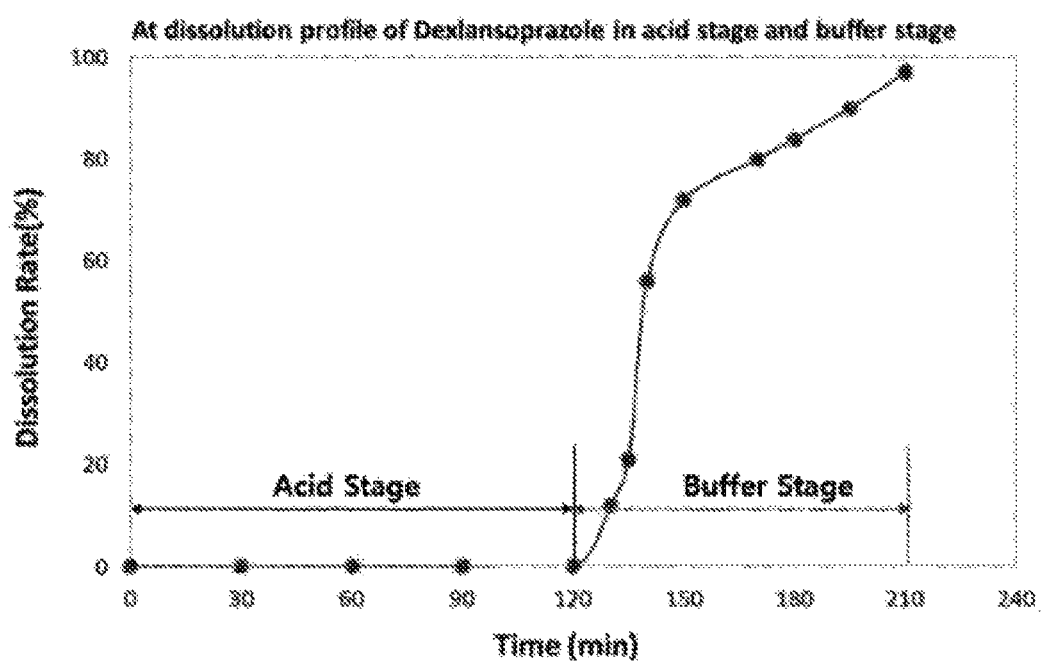

US 10,765,668 B2

ORAL TABLET COMPOSITION COMPRISING DEXLANSOPRAZOLE, ORAL TABLET COMPRISING THE SAME AND METHOD FOR MANUFACTURING THE SAME

TECHNICAL FIELD

The present invention relates to: an oral tablet composition comprising dexlansoprazole; an oral tablet comprising the same; and a method for manufacturing the same, and more particularly, to an oral tablet composition, which may be used to manufacture a tablet having improved hardness, disintegration time, and friability by comprising mannitol having a specific size, a disintegrating agent, and a lubricant together with amorphous dexlansoprazole; an oral tablet comprising the same; and a method for manufacturing the same.

BACKGROUND ART

Dexlansoprazole acts as a proton pump inhibitor (PPI) having actions such as a gastric acid secretion suppressive action or a gastric mucosal protective action, and has been widely used as a therapeutic agent for peptic ulcers, and the like.

However, the dexlansoprazole is poorly soluble in water and very unstable in acids, and thus is easily decomposed in gastric juice, which is an acidic solution. Further, pH affects the stability of dexlansoprazole in an aqueous solution state. Accordingly, for effective in vivo delivery of dexlansoprazole through oral administration, there is a need for a dosage form in which dissolution characteristics in the upper small intestine portion are improved while the loss of activity caused by gastric juice is minimized by enteric coating.

Thus, in the related art, a method for manufacturing a pharmaceutical formulation by coating a pharmaceutical formulation in a dosage form of a granule, pellet, tablet, or capsule with an enteric material or using a capsule comprising an enteric material has been used.

For example, Patent Document 1 (US 2011/0189271 A1) discloses a pharmaceutical formulation comprising: (a) a pharmacologically inert core; (b) a drug layer surrounding the core and comprising dexlansoprazole, or a salt thereof, and one or more pharmaceutically acceptable excipients; (c) an intermediate layer surrounding the drug layer; and (d) an enteric layer surrounding the intermediate layer. In this case, Patent Document 1 discloses that the dexlansoprazole or the salt thereof is amorphous, and the pharmaceutical formation may be formulated in a dosage form of a tablet or capsule.

In addition, Patent Document 1 describes a method for preparing the pharmaceutical formulation, comprising: (a) combining dexlansoprazole, a metal compound, and one or more pharmaceutically acceptable excipients with a solvent, to prepare a dexlansoprazole solution; (b) spraying the dexlansoprazole solution obtained in (a) onto a pharmacologically inert core; (c) spraying an intermediate layer onto the drug-coated core obtained in (b); and (d) spraying an enteric coating layer onto the intermediate layer-coated core obtained in (c).

Referring to the examples described in the above document, methods of processing a pharmaceutical formulation comprising dexlansoprazole into a pellet form through various steps and formulating the pharmaceutical formulation in the pellet form into a dosage form of a tablet or capsule are disclosed. However, according to the method, the amorphous raw material is recrystallized, so that the drug cannot be released as pure amorphous dexlansoprazole. In addition, when a tablet is prepared by using dexlansoprazole processed into the pellet form as in Patent Document 1, hardness may deteriorate or the disintegration time may be delayed, and friability is high, so that a problem in that the stability of the tablet deteriorates may also occur, and as the production process becomes complicated, there is a disadvantage in that the production efficiency deteriorates.

PRIOR ART DOCUMENT

Patent Document (Patent Document 1) US20110189271 A1

DISCLOSURE

Technical Problem

The present invention intends to provide an oral tablet composition, which may be used to manufacture a tablet having improved hardness, disintegration time, and friability by comprising mannitol having a specific size, a disintegrating agent, and a lubricant together with amorphous dexlansoprazole; and an oral tablet comprising the same.

Further, the present invention intends to provide a method for manufacturing an oral tablet, in which the production process is simplified using a dry direct compression method.

Technical Solution

To address the aforementioned problems, the present invention provides an oral tablet composition comprising amorphous dexlansoprazole, mannitol having an average particle size of 100 to 400 μm, a disintegrating agent and a lubricant.

The composition may comprise 0.1 to 20 wt % of the amorphous dexlansoprazole, 20 to 50 wt % of the mannitol, 25 to 55 wt % of the disintegrating agent, and 0.5 to 5 wt % of the lubricant.

The amorphous dexlansoprazole may have an average particle size of 0.1 to 15 μm.

The disintegrating agent may comprise one or more selected from the group consisting of microcrystalline cellulose, low-substituted hydroxypropyl cellulose, croscarmellose sodium, sodium starch glycolate, carboxymethyl cellulose sodium, carboxymethyl cellulose calcium, and crospovidone.

The lubricant may comprise one or more selected from the group consisting of magnesium stearate, stearic acid, zinc stearate, calcium stearate, sodium stearyl fumarate, talc, silicon dioxide, and colloidal silicon dioxide.

Meanwhile, the present invention provides an oral tablet comprising the oral tablet composition.

The friability of the oral tablet may be 0.01 to 0.5%.

In this case, the oral tablet may further comprise a core comprising the oral composition, an aqueous coating layer covering a surface of the core, and an enteric coating layer covering a surface of the aqueous coating layer.

The aqueous coating layer may comprise one or more selected from the group consisting of cellulose ether, polyvinylpyrrolidone, and polyvinyl alcohol, and the cellulose ether may comprise one or more selected from the group consisting of hydroxypropyl cellulose, hydroxypropyl methyl cellulose, hydroxymethyl cellulose, hydroxyethyl cellulose, hydroxybutyl cellulose, hydroxypentyl cellulose, and hydroxypropyl butyl cellulose.

The enteric coating layer may comprise one or more selected from the group consisting of hydroxypropyl methyl cellulose phthalate (HPMCP), hydroxypropyl methyl cellulose acetate succinate (HPMCAS), cellulose acetate phthalate, and derivatives thereof.

Further, the present invention provides a method for manufacturing the oral tablet, the method comprising: steps of (1) mixing amorphous dexlansoprazole, mannitol having an average particle size of 100 to 400 μm, and a disintegrating agent; (2) inputting and mixing a lubricant into the mixture obtained according to Step (1); and (3) compressing the mixture obtained according to Step (2).

The compression in Step (3) may be a dry direct compression method.

Moreover, the manufacturing method may further comprise: steps of coating the mixture compressed according to Step (3) with an aqueous coating layer; and coating a surface of the aqueous coating layer with an enteric coating layer.

Advantageous Effects

According to the present invention, it is possible to provide an oral tablet having excellent hardness, a shortened disintegration time, and at the same time improved friability by providing an oral tablet composition comprising mannitol having a specific size, a disintegrating agent, and a lubricant together with amorphous dexlansoprazole.

In addition, in the method for manufacturing an oral tablet according to the present invention, a dry direct compression method is used as the method for manufacturing the oral tablet, and thus an increase in production efficiency by simplifying the production process can be achieved.

Moreover, according to the present invention, the oral tablet was designed as a double-coated tablet to effectively suppress the drug from being released in the stomach and to release the drug in the intestines (pH 5.5 or more).

DESCRIPTION OF DRAWINGS

FIG. 1 is a graph illustrating the dissolution test results of the oral tablet manufactured according to Example 1.

MODES OF THE INVENTION

The present invention relates to an oral tablet composition comprising dexlansoprazole, an oral tablet comprising the same, and a manufacturing method thereof.

First, referring to an oral tablet composition, the composition includes amorphous dexlansoprazole, mannitol having an average particle size of 100 to 400 μm, a disintegrating agent, and a lubricant.

The amorphous dexlansoprazole is the main ingredient of the oral tablet according to the present invention, one of the proton pump inhibitors (PPIs) as described above, and has been widely used as a therapeutic agent for peptic ulcers. The dexlansoprazole is an optical isomer of lansoprazole, and is a compound represented by the following Chemical Formula 1.

Chemical Formula 1

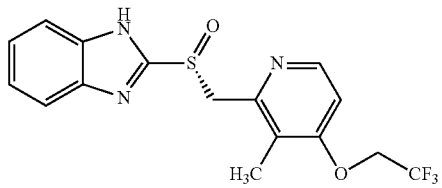

A content of the amorphous dexlansoprazole may be 0.1 to 20 wt % based on 100 wt % of the oral tablet composition, and when the content is less than 0.1 wt %, there is a risk that the efficacy is insignificant, whereas when the content is more than 20 wt %, the content exceeds a daily intake, so that there is a risk that a side effect due to the overdose occurs.

The amorphous dexlansoprazole may have an average particle size of 0.1 to 15 μm, and when the average particle size is less than 0.1 μm, there is a risk that the productivity deteriorates, whereas when the average particle size is more than 15 μm, there is a risk that the absorption rate in the body deteriorates.

As described above, it is possible to manufacture an oral tablet which is excellent in solubility and dissolution characteristics of the drug by using amorphous dexlansoprazole. However, the dexlansoprazole having such an amorphous form has poor flowability of the powder, so that a problem may occur during the compression into tablets, and the dexlansoprazole exhibits thermodynamically unstable characteristics under high temperature and humidity conditions, so that there is a disadvantage that it is difficult to mold the dexlansoprazole into wet granules. Thus, as a result of intensive studies to solve these problems, the present inventors confirmed that when mannitol having an average particle size of 100 to 400 μm is included together with amorphous dexlansoprazole, the flowability of an oral tablet composition including amorphous dexlansoprazole could be enhanced, and as a result, an oral tablet composition which is excellent in fluidity may be provided, thereby completing the present invention.

When the average particle size of the mannitol is out of a range of 100 to 400 μm, the flowability of the oral tablet composition comprising dexlansoprazole deteriorates and mixing uniformity deteriorates, so that filling properties are adversely affected, thereby adversely affecting content uniformity and tablet compression pressure.

A content of the mannitol may be 20 to 50 wt % based on 100 wt % of the oral tablet composition, and when the content is less than 20 wt %, there is a risk that an effect of contributing to improvement in flowability of the oral tablet composition including amorphous dexlansoprazole is insignificant, whereas when the content is more than 50 wt %, there is a risk that the disintegration time of the tablet is delayed or the dissolution rate thereof deteriorates.

The disintegrating agent (disintegrant) serves to facilitate breakup or disintegration of the solid dosage form after oral administration. The disintegrating agent may comprise one or more selected from the group consisting of microcrystalline cellulose, low-substituted hydroxypropyl cellulose, croscarmellose sodium, sodium starch glycolate, carboxymethyl cellulose sodium, carboxymethyl cellulose calcium, and crospovidone.

A content of the disintegrating agent may be 25 to 55 wt % based on 100 wt % of the oral tablet composition, and when the content is less than 25 wt %, there is a risk that the drug is poorly released in the body, whereas when the content is more than 55 wt %, there is a risk that it is difficult to maintain an appropriate hardness.

The lubricant serves to improve the fluidity of amorphous dexlansoprazole particles, prevent friction between the particles, and prevent amorphous dexlansoprazole particles from attaching to a tableting machine. The lubricant may comprise one or more selected from the group consisting of magnesium stearate, stearic acid, zinc stearate, calcium stearate, sodium stearyl fumarate, talc, silicon dioxide, and colloidal silicon dioxide.

A content of the lubricant may be 0.5 to 5.0 wt % based on 100 wt % of the oral tablet composition, and when the content is less than 0.5 wt %, the fluidity of amorphous dexlansoprazole particles is reduced and the particles may be attached to a tableting machine, so that compression may not be easily conducted. On the contrary, when the content of the lubricant is more than 5.0 wt %, the cohesive force of amorphous dexlansoprazole particles becomes weak, so that it is difficult to maintain an appropriate hardness, and a problem in that the disintegration time of the tablet is delayed and the dissolution rate deteriorates may be caused.

Meanwhile, the present invention provides an oral tablet comprising the oral tablet composition. The friability of the oral tablet may be 0.01 to 0.5%, and an oral tablet which is excellent in physical stability may be provided by having a friability within the range.

The oral tablet provided according to the present invention may further comprise a core comprising the oral composition, an aqueous coating layer covering a surface of the core, and an enteric coating layer covering a surface of the aqueous coating layer. By designing the oral tablet as a double-coated tablet as described above, since acid resistance is secured, the release of the drug in the stomach may be suppressed and the release of the drug in the intestines may be promoted, and accordingly, the drug-taking compliance of a patient may be improved.

The enteric coating layer is a coating layer disposed at the outermost portion of the oral tablet according to the present invention, and serves to suppress the drug from being released in the stomach. As used herein, "enteric" refers to a property in which disintegration and dissolution are not achieved under a gastric juice condition (around pH 1.2) for 2 hours and disintegration and dissolution are achieved under a small intestine condition (around pH 7.2) in a short period of time within 1 hour, and the enteric coating layer refers to a coating layer including a material having enteric properties.

The enteric coating layer may comprise one or more selected from the group consisting of hydroxypropyl methyl cellulose phthalate (HPMCP), hydroxypropyl methyl cellulose acetate succinate (HPMCAS), cellulose acetate phthalate, and derivatives thereof.

The aqueous coating layer is a coating layer present between a core comprising the oral tablet composition and the enteric coating layer, and serves to allow the enteric coating layer to be effectively and stably applied and minimize effects of dexlansoprazole on pH during the coating of the enteric coating layer.

The aqueous coating layer may comprise one or more selected from the group consisting of cellulose ether, polyvinylpyrrolidone, and polyvinyl alcohol. In this case, the cellulose ether may comprise one or more selected from the group consisting of hydroxyalkyl cellulose and hydroxyalkyl alkyl cellulose, and may preferably comprise one or more selected from the group consisting of hydroxypropyl cellulose, hydroxypropyl methyl cellulose, hydroxymethyl cellulose, hydroxyethyl cellulose, hydroxybutyl cellulose, hydroxypentyl cellulose, and hydroxypropyl butyl cellulose.

Further, the present invention provides a method for manufacturing the oral tablet, the method comprising: steps of (1) mixing amorphous dexlansoprazole, mannitol having an average particle size of 100 to 400 µm, and a disintegrating agent; (2) inputting and mixing a lubricant into the mixture obtained according to Step (1); and (3) compressing the mixture obtained according to Step (2).

The amorphous dexlansoprazole, the mannitol, the disintegrating agent, and the lubricant may be subjected to a sieving process in order to have a desired particle size.

The compression in Step (3) may be a dry direct compression method, and the production process may be simplified by using a dry direct compression method of directly compressing the mixture obtained according to Step (2), thereby enhancing the production efficiency. In addition, since the dry direct compression method is not used in the present invention, the crystal form of amorphous dexlansoprazole is not deformed during the process of manufacturing the oral tablet. Therefore, when amorphous dexlansoprazole is used as a raw material, the amorphous dexlansoprazole may be comprised as it is in an oral tablet to be finally obtained, and consequently, pure amorphous dexlansoprazole may be released in vivo. Accordingly, an oral tablet which is excellent in solubility and dissolution characteristics may be provided according to the present invention.

The method for manufacturing an oral tablet according to the present invention may further comprise: steps of coating the mixture compressed according to Step (3) with an aqueous coating layer; and coating a surface of the aqueous coating layer with an enteric coating layer. Accordingly, since a double-coated oral tablet is manufactured, acid resistance of the tablet may be secured and the drug-taking compliance of a patient may be enhanced.

Hereinafter, the present invention will be described in more detail with reference to examples, but the present invention is not limited to these examples.

Example 1

As described in Table 1, a first mixture was prepared by mixing 15.3 wt % of amorphous dexlansoprazole, 28.0 wt % of mannitol in the form of a granule, and 53.4 wt % of a disintegrating agent. In this case, the amorphous dexlansoprazole had an average particle size of 15 µm, and the mannitol in the form of a granule had an average particle size of 320 µm. Moreover, the disintegrating agent consists of 12.7 wt % of crospovidone, 25.4 wt % of sodium starch glycolate, and 15.3% of low-substituted hydroxypropyl cellulose.

Subsequently, a second mixture was prepared by inputting 3.3 wt % of a lubricant to the first mixture and mixing. In this case, the lubricant consists of 2.3 wt % of light anhydrous silicic acid and 1.0 wt % of magnesium stearate.

Subsequently, an oral tablet in the form of a tablet having a diameter of 1 cm was manufactured by compressing and tableting the second mixture with a tableting device (Keum-Sung Machinery Co., Ltd., KTSS).

Subsequently, the surface of the oral tablet was coated by spraying an aqueous coating layer onto the surface of the oral tablet. In this case, a coating composition used in the formation of an aqueous coating layer was prepared by inputting 6.7 wt % of hydroxypropyl methyl cellulose (HPMC) (Lotte Fine Chemical Co., Ltd., AN6) to 89.6 wt % of an aqueous ethanol solution (concentration of 10%) and dissolving, and then adding 0.7 wt % of a coating agent polyethylene glycol 6000 (Merck Millipore, PEG 6000) and 3.0 wt % of titanium dioxide (Sigma Aldrich, titanium (IV) oxide) thereto.

Subsequently, a tablet coated for oral use was manufactured by spray-coating the surface of the tablet coated with the aqueous coating layer with an enteric coating layer. In this case, a coating composition used in the formation of the enteric coating layer was prepared by inputting 7.8 wt % of hydroxypropyl methyl phthalate (Lotte Fine Chemical Co., Ltd., HPMCP HP-55) to 90.6 wt % of an aqueous ethanol solution (concentration of 10%) and dissolving, and then adding 0.8 wt % of a coating agent glycerin fatty acid ester (Mitsubishi, Polyglycerin esters) and 0.8 wt % of titanium dioxide (Sigma Aldrich, titanium (IV) oxide) thereto.

Examples 2 and 3 and Comparative Example 1

Oral tablets and tablets coated for oral use were manufactured in the same manner as in Example 1, except that mannitol having particle sizes described in the following Table 1 was used instead of the mannitol having an average particle size of 320 μm in the form of a granule.

<Evaluation Method>

1. Hardness (kp)

The hardness of each of the oral tablets manufactured according to Examples 1 to 3 and Comparative Example 1 was measured using a hardness meter (Pharma Test, PTB-311).

2. Friability (%)

The friability of each of the oral tablets manufactured according to Examples 1 to 3 and Comparative Example 1 was measured using a friability tester (Pharma Test, PTF-20ER).

3. Disintegration Time (Sec)

The disintegration time of each of the oral tablets manufactured according to Examples 1 to 3 and Comparative Example 1 was measured in accordance with the disintegration test method of the Korean Pharmacopoeia (11th Edition). Specifically, after the oral tablet was input to a test tube containing 900 ml of a phosphate buffer with a pH of 6.8, the disintegration time was evaluated as the time taken for the oral tablet to be completely disintegrated.

4. Dissolution Test

The dissolution rates of the tablets coated for oral use coated with the aqueous coating layer and the enteric coating layer were evaluated under the following conditions according to Examples 1 to 3 and Comparative Example 1, and the results thereof are illustrated in FIG. 1.

Dissolution method: Dissolution second method (paddle method) of the Korean Pharmacopoeia
Type of dissolution tester: manufacturer—ERWEKA GmbH, Type—DT 1420
Type of dissolution solution: pH1.2 (acid stage), pH7.2 (buffer stage)
Amount of dissolution solution: 900 mL
Temperature of dissolution solution: 37° C.
Paddle speed: 100 rpm In this case, after the dissolution test began in an aqueous solution with a pH of 1.2, 120 minutes later, the test was performed for a total of 210 minutes by changing the acid solution into a solution with a pH of 7.2, containing 5 mM sodium lauryl sulfate.

TABLE 1

| | | Example 1 | Example 2 | Example 3 | Comparative Example 1 |
|---|---|---|---|---|---|
| Dexlansoprazole (wt %) | | 15.3 | 15.3 | 15.3 | 15.3 |
| Mannitol (wt %) | Granule form (320 μm)$^a$ | 28.0 | — | — | — |
| | Powder form (210 μm)$^b$ | — | 28.0 | — | — |
| | Spray-dried form (125 μm)$^c$ | — | — | 28.0 | — |
| | Powder form (76 μm)$^d$ | — | — | — | 28.0 |
| Disintegrating agent (wt %) | Crospovidone | 12.7 | 12.7 | 12.7 | 12.7 |
| | Sodium starch glycolate | 25.4 | 25.4 | 25.4 | 25.4 |
| | Low-substituted hydroxypropyl cellulose | 15.3 | 15.3 | 15.3 | 15.3 |
| Lubricant (wt %) | Light anhydrous silicic acid | 2.3 | 23 | 2.3 | 2.3 |
| | Magnesium stearate | 1.0 | 1.0 | 1.0 | 1.0 |
| Hardness (kp) | | 18 | 20 | 14 | 9 |
| Friability (%) | | 0.12 | 0.14 | 0.25 | 0.48 |
| Disintegration time (sec) | | 48 | 42 | 60 | 128 |

* Dexlansoprazole: Amino Chemicals/Dexlansoprazole Amorphous
* Mannitol
$^a$(mannitol having an average particle size of 320 μm in the form of a granule): SPI Pharma/Granulated Mannogem
$^b$(mannitol having an average particle size of 210 μm in the form of powder): SPI Pharma/Pharmasperse ® 416
$^c$(spray-dried mannitol having an average particle size of 125 μm): SPI Pharma/Spray-dried Mannogem
$^d$(mannitol having an average particle size of 75 μm in the form of powder): SPI Pharma/Mannogem powder
* Crospovidone: Ashland/Polyplasdone XL
* Sodium starch glycolate: JRS/Sodium starch glycolate
* Low-substituted hydroxypropyl cellulose: ShinEtsu/L-HPC (LH-22)
* Light anhydrous silicic acid: Evonik/Aerosil 200 Pharma
* Magnesium stearate: Nitika/TABLUBE TM Referring to Table 1, it can be confirmed that in the case of the oral tablets comprising mannitol having an average particle size of 100 to 400 μm manufactured according to Examples 1 to 3, the hardness is excellent, the friability is low, and the disintegration time is short as compared to the oral tablet comprising mannitol having an average particle size of less than 100 μm manufactured according to Comparative Example 1.

Further, referring to FIG. 1, it can be confirmed that in the case of the tablet coated for oral use manufactured according to the present invention, the dissolution is suppressed in an acid state (pH 1.2) and the dissolution rate is rapidly increased in a buffered state (pH 7.2). From the confirmation, it can be seen that in the case of the tablet coated for oral use manufactured according to the present invention, the dissolution of dexlansoprazole is suppressed in the stomach and promoted in the intestines, and as a result, the tablet coated for oral use may be effectively delivered in vivo.

As described above, the examples disclosed in the present invention are provided not for limiting the technical spirit of the present invention, but for describing the technical spirit of the present invention, and the scope of the rights of the present invention should be interpreted by the following claims, and it should be interpreted in such a way that all the technical spirit within the equivalent scope of the present invention are included in the scope of the rights of the present invention.

The invention claimed is:

1. An oral tablet composition comprising:
   0:1 to 20 wt % amorphous dexlansoprazole,
   20 to 50 wt % mannitol having an average particle size of 100 to 400 m,
   25 to 55 wt % disintegrating agent selected from one or more of the group consisting of low-substituted hydroxypropyl cellulose, croscarmellose sodium, sodium starch glycolate, carboxymethyl cellulose sodium, carboxymethyl cellulose calcium, and crospovidone, and 0.5 to 5 wt % lubricant, wherein a friability of the oral tablet is 0.01 to 0.5%.

2. The oral tablet composition of claim 1, wherein the amorphous dexlansoprazole has an average particle size of 0.1 to 15 μm.

3. The oral tablet composition of claim 1, wherein the lubricant comprises one or more selected from the group consisting of magnesium stearate, stearic acid, zinc stearate, calcium stearate, sodium stearyl fumarate, talc, silicon dioxide, and colloidal silicon dioxide.

4. The oral tablet of claim 1, further comprising a core comprising the oral composition, an aqueous coating layer covering a surface of the core, and an enteric coating layer covering a surface of the aqueous coating layer.

5. The oral tablet of claim 4, wherein the aqueous coating layer comprises one or more selected from the group consisting of cellulose ether, polyvinylpyrrolidone, and polyvinyl alcohol.

6. The oral tablet of claim 5, wherein the cellulose ether comprises one or more selected from the group consisting of hydroxypropyl cellulose, hydroxypropyl methyl cellulose, hydroxymethyl cellulose, hydroxyethyl cellulose, hydroxybutyl cellulose, hydroxypentyl cellulose, and hydroxypropyl butyl cellulose.

7. The oral tablet of claim 4, wherein the enteric coating layer comprises one or more selected from the group consisting of hydroxypropyl methyl cellulose phthalate (HPMCP), hydroxypropyl methyl cellulose acetate succinate (HPMCAS), cellulose acetate phthalate, and derivatives thereof.

8. A method for manufacturing the oral tablet according to claim 1, the method comprising: steps of
 (1) mixing amorphous dexlansoprazole, mannitol having an average particle size of 100 to 400 pm, and a disintegrating agent;
 (2) inputting and mixing a lubricant into the mixture obtained according to Step (1); and
 (3) compressing the mixture obtained according to Step (2).

9. The method of claim 8, wherein the compression in Step (3) is a dry direct compression method.

10. The method of claim 8, further comprising: steps of coating the mixture compressed according to Step (3) with an aqueous coating layer; and coating a surface of the aqueous coating layer with an enteric coating layer.

* * * * *